United States Patent [19]

Sarpotdar et al.

[11] Patent Number: 4,732,892
[45] Date of Patent: Mar. 22, 1988

[54] L-α-AMINO ACIDS AS TRANSDERMAL PENETRATION ENHANCERS

[75] Inventors: Pramod P. Sarpotdar, Audubon; James L. Gaskill, Devon; Robert P. Giannini, East Norriton; Charles R. Daniels, Erdenheim, all of Pa.

[73] Assignee: American Home Products Corporation, New York, N.Y.

[21] Appl. No.: 754,805

[22] Filed: Jul. 12, 1985

[51] Int. Cl.$^4$ ............................................. A61K 31/56
[52] U.S. Cl. .................................... 514/178; 514/171; 514/179; 514/561; 514/843; 514/947
[58] Field of Search ................ 514/171, 561, 178, 179

[56] References Cited

U.S. PATENT DOCUMENTS

| | | | |
|---|---|---|---|
| 3,527,864 | 9/1970 | Kilmer et al. | 424/177 |
| 3,787,571 | 1/1974 | Higuchi | 424/239 |
| 3,989,816 | 11/1976 | Rajadhyaksha | 424/60 |
| 4,258,037 | 3/1981 | Juvin | 514/561 X |
| 4,362,737 | 12/1982 | Schafer et al. | 514/171 |
| 4,409,233 | 10/1983 | Tsukada et al. | 514/561 X |
| 4,537,776 | 8/1985 | Cooper | 514/171 |

*Primary Examiner*—Leonard Schenkman
*Attorney, Agent, or Firm*—Arthur G. Siefert

[57] ABSTRACT

The disclosed invention provides methods and compositions utilizing L-α-amino acids for enhancing the rate of penetration through the skin of both topical medicaments and of drugs employed for systemic administration. Fifteen L-α-amino acids were tested and found to enhance the rate of penetration of levonorgestrel through hairless mouse skin. These were Tryptophan, Glutamic Acid, Glycine, Proline, Alanine, Serine, Arginine, Aspartic Acid, Leucine, Isoleucine, Cysteine, Valine, α-Aminobutyric Acid, Norvaline and Norleucine. The effect of pH on the rate of penetration of the various amino acids was also examined and found to be unpredictable overall.

8 Claims, No Drawings

L-α-AMINO ACIDS AS TRANSDERMAL PENETRATION ENHANCERS

This invention provides a method and pharmaceutical compositions for enhancing the rate of penetration of drugs or medications through the skin. The enhanced rate of transdermal penetration provided by the invention is attained by including in the transdermal drug delivery system an amount of an L-α-amino acid. The invention also comprises transdermal drug delivery systems containing an L-α-amino acid as a penetration enhancer. Preferred L-α-amino acids useful for enhancing the rate of penetration in transdermal drug delivery systems are Tryptophan, Alanine, Arginine, Proline, Serine, Aspartic Acid, Cysteine, Glutamic Acid, Glycine, Isoleucine, Leucine, Valine, α-Aminobutyric Acid, Norvaline and Norleucine. Particularly preferred L-α-amino acids are Valine, Cysteine, Leucine, Isoleucine, α-Aminobutyric Acid, Norvaline and Norleucine.

BACKGROUND OF THE INVENTION

A low rate of penetration of drug through the skin is one of the major obstacles to the development of transdermal delivery systems. In many cases, the area of the skin which must be in contact with drug is prohibitively large unless the rate of penetration is increased.

Various compounds or compositions have been found to increase the rate of penetration of particular drugs. For example, U.S. Pat. No. 3,527,864 discloses that dimethylsulfoxide and homologous low molecular weight sulfoxides, when used in solvent concentrations, e.g. 50 percent or more, enhance the rate of penetration of various substances. However, these low molecular weight sulfoxides are absorbed systemically where they cause undesireable side effects. Said U.S. Pat. No. 3,527,864 claims the use of higher molecular weight ($C_8$–$C_{13}$) sulfoxides in amounts of 0.1 to 10.0 percent by weight to enhance the penetration of various antimicrobial agents used for topical treatment.

U.S. Pat. No. 3,989,816 describes further agents useful for enhancing the rate of penetration of various topical medications or cosmetics. These agents are 1-substituted azacycloheptan-2-ones. Among these agents is 1-dodecyl-azacyclopentan-2-one, known as azone, which has found wide use in enhancing the rate of penetration through the skin of various medicaments. U.S. Pat. No. 3,787,571 describes the use of trichloroethanol and trifluoroethanol to enhance the rate of penetration of drugs and medications through the skin.

Applicants' invention provides means and compositions utilizing L-α-amino acids for enhancing the rate of penetration through the skin of both topical medicaments and of drugs employed for systemic administration.

DETAILED DESCRIPTION OF THE INVENTION

This invention provides a pharmaceutical composition for transdermal delivery of a drug or medication (active ingredient) comprising an active ingredient and an amount of an L-α-amino acid effective to enhance the rate of penetration of said active ingredient through the skin, dispersed in a transdermally effective carrier. The preferred L-α-amino acids are Tryptophan, Glutamic Acid, Glycine, Proline, Alanine, Serine, Arginine, Aspartic Acid, Leucine, Isoleucine, Cysteine, Valine, α-Aminobutyric Acid, Norvaline and Norleucine. Of these Valine, Cysteine, Isoleucine, Leucine, α-Aminobutyric Acid, Norvaline and Norleucine are especially preferred. The preferred transdermally effective carrier comprises a non-polymeric matrix formed from a metal salt of a fatty acid. Sodium or potassium stearate are preferred salts of a fatty acid for forming such non-polymeric matrices. An "active ingredient" may be a drug or medication for systemic delivery or for topical treatment of conditions of the skin, including cosmetics. Preferred active ingredients for enhanced transdermal delivery according to the invention are those listed in Table A below. Levo-norgestrel is particularly preferred for application of this invention. Also preferred are Ethinyl Estradiol and 17-Beta-estradiol.

This invention further provides a method for enhancing the rate of penetration through the skin of an active ingredient contained in a pharmaceutical composition for transdermal delivery of a drug or medication comprising such active ingredient dispersed in a transdermally effective carrier, said method characterized in including in said composition an amount of an L-α-amino acid effective for enhancing the rate of penetration of said active ingredient through the skin. The preferred and especially preferred L-α-amino acids listed above with respect to the composition of the invention are also preferred and especially preferred for the method aspect of the invention. Also preferred for the method aspect of the invention is a carrier which comprises a non-polymeric matrix formed from a metal salt of a fatty acid. Sodium or potassium stearate are such preferred metal salts of a fatty acid.

A further aspect of the invention provides a pharmaceutical composition for the transdermal delivery of the active ingredients Levo-norgestrel, Ethinyl Estradiol or 17-Beta-estradiol comprising such active ingredient and an amount of an L-α-amino acid effective for enhancing the rate of penetration through the skin of such active ingredient, dispersed in a transdermally effective carrier. The preferred and particularly preferred L-α-amino acids listed above and the non-polymeric matrix carrier described above are also preferred for this aspect of the invention.

As noted in the Examples below, the enhanced rate of penetration provided by the L-α-amino acids is generally not pH dependent, although certain amino acids, when used with Levo-norgestrel, performed best at particular pH's. Thus, the rate enhancement with a given active ingredient and amino acid may be effective over a wide range of pH's, for example pH 2 to 11. However, due to skin irritation, a preferred range of pH's is 3.5 to 9, and a more preferred range of pH's is 5 to 8.

A transdermal dosage form of the present invention is preferably formed as follows. First a measured amount of the amino acid(s) of choice is dissolved in water (the concentration in water ranges from 0.01 to 1.0 molar, the preferred range being 0.06 to 0.4 molar) and the pH is adjusted to the desired value with either hydrochloric acid or sodium hydroxide, as described below. Then an appropriate amount of sodium stearate is added (the concentration ranges from 1.0 to 25% w/w, the preferred range being 3 to 9% w/w). This mixture is heated until the sodium stearate is dissolved. To this is added the required amounts of active ingredient and alcohol, USP (the concentration may range from 0 to 50% w/w, the preferred range being 20 to 40% w/w). The composition is then poured into suitable molds and cooled to form a flexible matrix.

The cooled matrix is removed from the mold and, if desired, pressed into contact with an adhesive dispersed on an occlusive (that is, totally closed) backing of an impervious material, such as aluminum foil. The backing may have a flange area which extends around the outer periphery of the matrix. An adhesive may be applied to the flange area for attachment to the skin. A foil-backed paper is adhered to the flange and covers the face of the matrix as a release liner after manufacture and prior to use. As an alternative, a non-rate-controlling foraminous membrane may be applied over the face of the matrix and attached to the adhesive of the flanges. A second adhesive layer may be applied to this membrane for attachment to the skin, and a release liner adhered as above.

In case where a non rate limiting foraminous membrane is used, the gelling agent (sodium stearate or the like) can be entirely eliminated. A solution or suspension of active ingredient(s) in various solvents with the amino acids of the present invention and/or other penetration enhancing agents as well as other pharmaceutical aids may be used.

In addition to the amino acid, other compounds may be included in the formula to provide even further enhancement of the penetration of the active ingredient through the skin, for example, propylene glycol and glycerine in a ratio of about 1:1 to 1:5 of each other (w/w), trichloroethanol, trifluoroethanol, dimethylsulfoxide, or azone.

The matrix described above is non-polymeric. The preferred gelling agent for such matrix is sodium stearate, but other alkaline metal salts of fatty acids also may be used, such as sodium caprylate, sodium laurate, sodium myristate, sodium palmitate, sodium oleate, sodium stearate, potassium caprylate, potassium laurate, potassium myristate, potassium palmitate, potassium oleate, and the corresponding salts with calcium, magnesium, aluminum, zinc, and other metals.

While the present invention has been described with regard to the use of a non-polymeric transdermal dosage form, it is to be understood that the principles of this invention can also be applied to polymeric transdermal dosage forms. The ambit of the invention extends to all transdermal dosage forms in which the ingredients are compatible.

The rate of penetration enhancement of the present invention due to the amino acids is not limited to the presence of an alkaline metal stearate but may be achieved with other transdermal dosage form embodiments in which the amino acids may be dispersed in other types of carrier matrices. These include other non-polymeric and polymeric matrices as well as porous polymeric membranes composed of polyacrylates, polymethacrylates, polyvinyl alcohols, polyvinylpyrrolidone, silicones and the like. For example, such membranes and matrices are discussed in the following articles:

(1) Y. Chien, *Pharm. Tech.*, vol. 9, no. 5, page 50, 1985.
(2) M. Wolff, G. Cordes and V. Luckow, *Pharm. Res.*, page 23, 1985.
(3) D. Hsieh, C. Chiang and D. Desai, *Pharm. Tech.*, vol. 9, No. 6, page 39, 1985.
(4) P. Keshary, and Y. Chien, *Drug Development and Ind. Pharm.*, vol. 10, No. 10, page 1663, 1984.
(5) N. Parikh, A. Babar and F. Plakogiannis, *Pharm. Acta. Helv.*, vol. 60, No. 2, page 34, 1985.
(6) Y. W. Chien, P. K. Keshary, Y. Huang and P. P. Sarpotdar, *J. Pharm. Sci.*, vol. 72, no. 8, pages 968–970, 1983.
(7) S. K. Chandrasekaran, *Drug Development and Ind. Pharm.*, vol. 9, No. 4, pages 627–646, 1983.
(8) L. R. Laufer et al., *Am. J. Obstet. Gynecol.*, vol. 146, No. 5, page 533, 1983.
(9) H. Groth, *J. Hyperten.*, 1 (suppl.), page 120, 1983.

Such membranes and matrices suitable for transdermal delivery dosage forms are also described in the following U.S. Pat. Nos. 3,598,122; 3,598,123; 4,031,894; 4,060,084; 4,201,211; 4,314,557; 4,293,565; 4,306,551; 4,307,717; 4,125,110; 4,274,420; 4,321,252; 4,291,015; 3,992,518 and 4,053,580.

Additionally, liquid carrier solutions, comprising an appropriate solvent or cosolvents, the active ingredient(s) and the rate enhancing L-α-amino acid, and, optionally another rate-ennhancing agent, may be used in place of a matrix or solid form delivery system. Such liquid form may also be in the form of a suspension. These may be applied in the form of patches as described above or as otherwise known in the art.

A list of therapeutic classes and some specific examples of drugs suitable for incorporation into this invention is provided in Table A. The invention is not limited in application to levonorgestrel, which is exemplified below, or solely to those drugs noted in Table A.

TABLE A

| Therapeutic Category | Active Ingredient |
| --- | --- |
| Non-Steroidal Anti-inflammatory | Indomethacin |
| Beta-Blocker | Propranolol |
| Sedative/Anticonvulsant | Phenobarbital |
| Local Anesthetic | Novocaine |
|  | Benzocaine |
|  | Xylocaine |
| Antifungal | Gentamycin |
|  | Amphotericin B |
| Antihypertensive | Clonidine |
|  | Nitroglycerin |
|  | Guanabenz |
| Steroidal Contraceptives | Ethinyl Estradiol |
|  | Levo-norgestrel |
|  | 17-Beta-estradiol |
| Antiarrhythmic | Verapamil |

The size of the dosage form, or patch, depends on the therapeutic dose per unit time and on the penetration rate of the active ingredient through the skin. A patch area of about 30 square centimeters ($cm^2$) or less is considered desirable. Therefore penetration rate is a major consideration.

The dosage form may contain from about 1 to 50 percent by weight an active ingredient to provide the optimum transdermal dosage. The optimum dosage is determined by pharmacodynamic and pharmacokinetic studies of the active ingredient. Such studies are described in *Fundamentals of Clinical Pharmacokinetics* by John Wagner, first edition, 1975, Drug Intelligence Publications Inc., Hamilton, Illinois and *Pharmacokinetics*, by Milo Gibaldi and Donald Perrier, First Edition, 1975, published by Marcel Dekker.

The following examples illustrate the manner and mode of carrying out the invention. As stated above, the invention is not limited to these examples. Examples 1-34 illustrate the making of different solutions of the L-α-amino acid/levonorgesrel drug delivery system utilized for experimental purposes. Example 35 describes the procedure for measuring rates of penetration and gives the results of this procedure with the amino acid/levonorgestrel solutions of Examples 1-34. Example 35 also describes further tests and results relating the effects of varying pH's on the ability of the different α-amino acids to enhance the rate of penetration of Levo-norgestrel. These results are shown in Tables I-IX of Examples 35.

In the examples, the steady state rate of penetration, or flux, is indicated by the symbol: Jss. The cumulative amount of drug penetrated is indicated by the Symbol: Q. The lag period to reach steady state is indicated by the symbol: $t_L$. The standard deviation for statistical purposes is abbreviated: S.D. The standard error of the mean for statistical purposes is abbreviated S.E.M. Abbreviation "g" denotes grams, "mg" denotes milligram, "mcg" denotes micrograms and "ng" denotes nanograms.

EXAMPLE 1

An amino acid/levonorgestrel solution (pH=4.0) was prepared by first placing 0.500 g of L-(−)-Tryptophan in enough distilled water to give a final volume of 50 ml. The solution was filtered through a 5 μm Millex ® filter. The pH of this solution was adjusted to 4.0 with 0.1N HCl. To 1.485 g of the amino acid solution was added 1.485 g of a mixture of ethanol and distilled water (previously prepared with 84.2 g of Alcohol U.S.P. and 15.8 g of distilled water). To 2.97 g of the ethanolic amino acid solution was added 0.030 g of $^{14}$C-labeled levonorgestrel (total acitivity=10.5 μCi) to give a final concentration of levonorgestrel of 1% w/w.

EXAMPLE 2

An amino acid/levonorgestrel solution (pH=4.0) was prepared by first placing 1.782 g of L-Alanine in enough distilled water to give a final volume of 50 ml. The pH of this solution was adusted to 4.0 with 0.1N HCl. To 10.0 ml of the amino acid solution was added 8.0 ml of Ethanol (absolute) and 2.0 ml of distilled water. A 2.97 g portion of this solution was then mixed with 0.030 g of $^{14}$C-labeled levonorgestrel (total activity=10.5 μCi), to give a final concentration of levonorgestrel of 1% w/w.

EXAMPLE 3

An amino acid/levonorgestrel solution (pH=4.0) was prepared by first placing 3.484 g of L-(+)-Arginine in enough distilled water to give a final volume of 50 ml. The pH of this solution was adjusted to 4.0 with 0.1N HCl. To 1.485 g of the amino acid solution was added 1.485 g of a mixture of ethanol and distilled water (previously prepared with 84.2 g of Alcohol U.S.P. and 15.8 g of distilled water). To the ethanolic amino acid solution was added 0.030 g of 14C-labeled levonorgestrel (total activity=10.5 μCi).

EXAMPLE 4

An amino acid/levonorgestrel solution (pH=4.0) was prepared as in Example 3 but using 2.303 g of L-(−)-Proline in place of L-(+)-Arginine.

EXAMPLE 5

An amino acid/levonorgestrel solution (pH=4.0) was prepared as in Example 2 but using 2.102 g of L-(−)-Serine in place of L-Alanine.

EXAMPLE 6

An amino acid/levonorgestrel solution (pH=4.0) was prepared as in Example 1 but using 0.225 g of L-(+)-Aspartic Acid in place of L-(−)-Tryptophan.

EXAMPLE 7

An amino acid/levonorgestrel solution (pH=4.0) was prepared as in Example 3 but using 2.423 g of L-(+)-Arginine.

EXAMPLE 8

An amino acid/levonorgestrel solution (pH=4.0) was prepared as in Example 1 but using 0.425 g of L-Glutamic Acid in place of L-(−)-Tryptophan.

EXAMPLE 9

An amino acid/levonorgestrel solution (pH=4.0) was prepared as in Example 2 but using 1.501 g of L-Glycine in place of L-Alanine.

EXAMPLE 10

An amino acid/levonorgestrel solution (pH=4.0) was prepared as in Example 2 but using 1.311 g of L-(+)-Isoleucine in place of L-Alanine.

EXAMPLE 11

An amino acid/levonorgestrel solution (pH=4.0) was prepared as in Example 2 but using 1.311 g of L-Leucine in place of L-Alanine.

EXAMPLE 12

An amino acid/levonorgestrel solution (pH=4.0) was prepared as in Example 2 but using 2.343 g of L-(+)-Valine in place of L-Alanine.

EXAMPLE 13

An amino acid/levonorgestrel solution (pH=2.4) was prepared by first placing 2.343 g of L-(+)-Valine in enough distilled water to give a final volume of 50 ml. The pH of this solution was adjusted to 2.4 with 0.1N HCl. To 25.0 ml of the amino acid solution was added 21.0 ml of Alcohol U.S.P. and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 14

An amino acid/levonorgestrel solution (pH=5.9) was prepared by first placing 2.343 g of L-(+)-Valine in enough distilled water to give a final volume of 50 ml. The pH of this solution was adjusted to 5.9 with 0.1N NaOH. To 25.0 ml of the amino acid solution was added 21.0 ml of Alcohol U.S.P. and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 15

An amino acid/levonorgestrel solution (pH=9.6) was prepared by first placing 2.343 g of L-(+)-Valine in enough distilled water to give a final volume of 50 ml. The pH of this solution was adjusted to 9.6 with 0.1N NaOH. To 25.0 ml of the amino acid solution was added 21.0 ml of Alcohol U.S.P. and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 16

An amino acid/levonorgestrel solution (pH=2.4) was prepared as in Example 13 but using 1.311 g of L-Leucine in place of L-(+)-Valine.

EXAMPLE 17

An amino acid/levonorgestrel solution (pH=6.0) was prepared by first placing 1.311 g of L-Leucine in enough distilled water to give a final volume of 50 ml. The pH of this solution was adjusted to 6.0 with 0.1N NaOH. To 25.0 ml of the amino acid solution was added 21.0 ml of Alcohol U.S.P. and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 18

An amino acid/levonorgestrel solution (pH=9.7) was prepared by first placing 1.311 g of L-Leucine in enough distilled water to give a final volume of 50 ml. The pH of this solution was adjusted to 9.7 with 0.1N NaOH. To 25.0 ml of the amino acid solution was added 21.0 ml of Alcohol U.S.P. and the volume brought up to 50 ml with distilled water after checking and readjusting pH if necessary. A 2.97 g portion of this solution was then mixed with 0.030 g of $^{14}$C-labelled levonorgestrel (total activity=10.5 μCi).

EXAMPLE 19

An amino acid/levonorgestrel solution (pH=2.4) was prepared by first placing 1.311 g of L-(+)-Isoleucine in enough distilled water to give a final volume of 50 ml. The pH of this solution was adjusted to 2.4 with 0.1N HCl. To 25.0 ml of the amino acid solution was added 20.0 ml of Ethanol (absolute) and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 20

An amino acid/levonorgestrel solution (pH=6.0) was prepared by first placing 1.311 g of L-(+)-Isoleucine in enough distilled water to give a final volume of 50 ml. The pH of this solution was adjusted to 6.0 with 0.1N NaOH. To 25.0 ml of the amino acid solution was added 20.0 ml of Ethanol (absolute) and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 21

An amino acid/levonorgestrel solution (pH=9.7) ws prepared by first placing 1.311 g of L-(+)-Isoleucine in enough distilled water to give a final volume of 50 ml. The pH of this solution was adjusted to 9.7 with 0.1N NaOH. To 25.0 ml of the amino acid solution was added 20.0 ml of Ethanol (absolute) and the volume brought up to 50 ml with distilled water after checking and readjusting pH if necessary. A 2.97 g portion of this solution was then mixed with 0.030 g of $^{14}$C-labeled levonorgestrel (total activity=10.5 μCi).

EXAMPLE 22

An amino acid/levonorgestrel solution (pH=2.4) was prepared as in Example 19 but using 1.501 g of L-Glycine in place of L-(+)-Isoleucine.

EXAMPLE 23

An amino acid/levonorgestrel solution (pH=6.0) was prepared as in Example 20 but using 1.501 g of L-Glycine in place of L-(+)-Isoleucine.

EXAMPLE 24

An amino acid/levonorgestrel solution (pH=9.7) was prepared as in Example 21 but using 1.501 g of L-Glycine in place of L(+)-Isoleucine.

EXAMPLE 25

To 2.985 g of a 40% w/w solution of ethanol in distilled water was added 0.015 g of $^{14}$C-labeled levonorgestrel (total activity=4.5 μCi).

EXAMPLE 26

An amino acid solution (pH 2.38) was prepared by first placing 0.328 g of L-Norleucine in enough distilled water to give a final volume of 25 mL. The pH of this solution was adjusted to 2.38 with 1.0N HCl. To 1.500 g of amino acid solution was added 1.200 g of absolute alcohol and 0.270 g of distilled water. To the ethanolic amino acid solution was added 0.30 g of $^{14}$C-levonorgestrel (total activity=11.55 μCi) to give the final concentration of levonorgestrel of 1% w/w.

EXAMPLE 27

An amino acid solution (pH 6.09) was prepared by first placing 0.328 g of L-Norleucine in enough distilled water to give a final volume of 25 mL. The pH of this solution was adjusted to 6.09 with 0.1N NaOH. To 1.500 g of amino acid solution was added 1.200 g of absolute alcohol and 0.270 g of distilled water. To the ethanolic amino acid solution was added 0.030 g of $^{14}$C-levonorgestrel (total activity=11.55 μCi) to give a final concentration of levonorgestrel of 1% w/w.

EXAMPLE 28

An amino acid solution (pH 9.73) was prepared by first placing 0.328 g of L-Norleucine in enough distilled water to give a final volume of 25 mL. The pH of this solution was adjusted to 9.73 with 1.0N NaOH. To 1.500 g of amino acid solution was added 1.200 g of absolute alcohol and 0.270 g of distilled water. To the ethanolic amino acid solution was added 0.030 g of $^{14}$C-levonorgestrel (total activity - 11.55 μCi) to give the final concentration of levonorgestrel of 1% w/w.

EXAMPLE 29

An amino acid/levonorgestrel solution (pH 2.37 was prepared as in Example 27 but using 1.172 g of L-Norvaline in place of L-Norleucine.

EXAMPLE 30

An amino acid/levonorgestrel solution (pH 5.96) was prepared as in Example 28 but using 1.172 g of L-Norvaline in place of L-Norleucine.

EXAMPLE 31

An amino acid/levonorgestrel solution (pH 9.76) was prepared as in Example 29 but using 1.172 g of L-Norvaline in place of L-Norleucine.

EXAMPLE 32

An amino acid/levonorgestrel solution (pH 2.29) was prepared as in Example 27 but using 1.031 g of L-α-Amino-n-Butyric Acid in place of L-Norleucine.

EXAMPLE 33

An amino acid/levonorgestrel solution (pH 6.03) was prepared as in Example 28 but using 1.031 g of L-α-Amino-n-Butyric Acid in place of L-Norleucine.

EXAMPLE 34

An amino acid/levonorgestrel solution (pH 9.82) was prepared as in Example 29 but using 1.031 g of L-α-Amino-n-Butyric Acid in place of L-Norleucine.

EXAMPLE 35

Measurement of Rates of Penetration

Initially, twelve amino acids were selected for evaluation of their effect on the rate of penetration of levonorgestrel through hairless mouse skin. Differing amino acids were selected according to the structure of their side chain so that at least one amino acid from each of the seven different chemical groups was studied. These were Trytophan, Alanine, Arginine, Proline, Serine, Aspartic Acid, Cysteine, Glutamic Acid, Glycine, Isoleucine, Leucine, and Valine. Tables I–VIII below deal with these 12 amino acids. These were incorporated into transdermal drug formulations and the corresponding rates of penetration were determined. These 12 amino acids were tested at various pHs; $pK_1' = 2.2-3.2$, $pH = 4.2-4.9$, $pH_{ISO} = 5.7-6.7$ (glutamic acid $pH_{ISO} = 3.8$ and arginine $pH_{ISO} = 10.8$) and $pK_2 = 8.6-10.8$. A total of 36 out of a possible 48 formulations were evaluated. The effect of amino acid, pH and ionic species on the rate of penetration was then analyzed.

The amino acids were dissolved in distilled water and the pH was adjusted by addition of either 0.1 or 1.0N HCl or 1.0N NaOH. Ethanol was then added to give a final ethanol concentration of 40% w/w. The pH was monitored and recorded. Generally a shift of approximately 0.5 units was noticed. 1%(w/w) levonorgestrel was suspended in this solvent system. Suspensions were applied to hairless mouse skin as described above.

The penetration of drug across hairless mouse skin was studied in vitro using a modified Franz diffusion cell apparatus as described by Y. W. Chien, P. R. Keshary, Y. C. Huany and P. P. Sarpotdar in "Comparative Controlled Skin Permeation of Nitroglycerin from Marketed Transdermal Delivery Systems," J. Pharmaceutical Sciences, Vol. 72, No. 8 August 1983, pp. 968–970. Approximately, 0.5 ml of each of the mixtures described in the above examples was applied to each of 4 hairless mouse skins on 4 different Franz diffusion cells. Samples were withdrawn at predetermined times up to a total of 10 hours. The results of various measurements of rates are shown in Tables I–VIII below.

In Table I the penetration enhancement is shown at varying concentrations of amino acid in the mixture and at varying pH's. It can be seen from the Table I that the 12 amino acids tested enhance the rate of penetration of levonorgestrel across the hairless mouse skin when compared to the water/ethanol control solution. It is interesting to note that when pH is held between 4.0 and 5.0 L-Glutamic Acid, L-(+)-Isoleucine and L-Leucine give relatively high rates of penetration for levonorgestrel even though their concentration in solution is lower than many of the amino acids. It should also be noted that for some of the amino acids tested there appears to be an effect of pH. This effect however is not of the same magnitude or direction for all of the amino acids. The relationship between pH and the degree of penetration enhancement caused by any particular amino acid is thus not well understood nor can it be predicted from theory at this time.

The various amino acids and the corresponding overall rates of penetration of levonorgestrel (average of all data at all pH values) are listed in Table II. An initial 0.2M concentration for all the amino acids was chosen. Lower concentrations were necessary for some of the amino acids due to limited aqueous solubility. In previous experimentation, a hundred-fold difference in the concentration of Glycine buffer was tested. This resulted in no significant difference in the rate of penetration. Therefore, it was assumed that the differing concentrations used in this work would not affect the penetration rate.

Comparing the observed penetration rates shows that valine, cysteine, isoleucine and leucine formulations provided the highest rates. The valine formulation had the overall best rate, although there is a lack of any significant difference within this group (P = 0.05). The amino acids were further compared at specific pHs (Tables III–VI). The same four, valine, cysteine, isoleucine, and leucine seem to have the greatest affect on penetration.

In the pH range of 2.3 to 3.2, approximately equal to the $pK_1'$, cysteine provided a significantly increased rate (Table III). Next in rank to cysteine were leucine, valine and isoleucine. When the amino acids were tested at pH 4.2–4.9 there was no significant difference in rate of penetration (Table IV). It should be noted that valine, leucine and isoleucine provided the fasted rates at this pH. Isoleucine provided the fasted rate of those tested at their isoelectric pH (approx. 5.7–6.7)(Table V). This rate was followed by the corresponding rates for valine and leucine. Cysteine was not tested at this pH. Valine, cysteine, and leucine had the fastest rate of penetration of those amino acids tested at $pK_2'$ (pH = 8.6–10.8) (Table VI). Comparing these three amino acids at this pH level there was an absence of statistical difference.

The various pH values used in this study produced a range of average net charge for each individual amino acid. Analysis was performed which compared the affect of amino acid average net charge on the rate of penetration of levonorgestrel (Table VII a, b, c). A dibasic amino acid, such as glycine, can exist in three species having average net charges of +1, 0 or −1. For a tribasic amino acid such as glutamic acid, four species can exist, having average net charges of +1, 0, −1 or −2. Concentration of each species is pH and pKa dependent for each amino acid. Through the use of the Henderson Hasselbach equation, pH = pKa + log (salt/acid), the percent of ionic species were determined. A lack of any noticable correlation of charge with penetration rate was observed given the presently available data. This data is recorded in Tables VII, a, b, and c.

In Table VIII the average flux of levonorgestrel over all amino acids at individual pH values are shown. For this particular analysis, effect or trend of an individual amino acid was ignored. It appears that levonorgestrel rates of penetration are not affected significantly by changing pH when an amino acid is present in the formulation.

Subsequently, rates of penetration were also determined (in hairless mouse skin a described above) for Norleucine, Norvaline and α-Amino-n-Butyric Acid. These results are shown in Table IX.

TABLE I

Effect of Amino Acids in the Solvent System on the Steady State Rate of Penetration of Levonorgestrel through Hairless Mouse Skin

| Example Number | Amino Acid | Concentration | Final pH | $J_{ss}$ (mcg/cm²/hr) ± SE | Lag (hrs) ± SE |
|---|---|---|---|---|---|
| 1 | L-(−)-Tryptophan | 0.03 m* | pH 4.7 | 0.6020 ± 0.089 | 3.5 ± 0.14 |
| 2 | L-(+)-Alanine | 0.2 m | pH 4.8 | 0.8553 ± 0.085 | 2.7 ± 0.25 |
| 3 | L-(+)-Arginine | 0.2 m | pH 4.2 | 0.9590 ± 0.265 | 3.4 ± 0.11 |
| 4 | L-(−)-Proline | 0.2 m | pH 4.6 | 1.0863 ± 0.161 | 3.2 ± 0.23 |
| 5 | L-(−)-Serine | 0.2 m | pH 4.7 | 1.1287 ± 0.134 | 2.3 ± 0.31 |
| 6 | L-(+)-Aspartic Acid | 0.2 m | pH 4.4 | 1.1538 ± 0.185 | 2.9 ± 0.14 |
| 7 | L-(+)-Cysteine | 0.2 m | pH 4.9 | 1.1635 ± 0.092 | 2.9 ± 0.08 |
| 8 | L-Glutamic Acid | 0.03 m* | pH 4.6 | 1.1910 ± 0.227 | 3.4 ± 0.09 |
| 9 | Glycine | 0.2 m | pH 4.7 | 1.2790 ± 0.284 | 3.3 ± 0.20 |
| 10 | L-(+)-Isoleucine | 0.1 m | pH 4.5 | 1.3328 ± 0.276 | 3.1 ± 0.18 |
| 11 | L-Leucine | 0.1 m | pH 4.4 | 1.4451 ± 0.358 | 2.5 ± 0.33 |
| 12 | L-(+)-Valine | 0.2 m | pH 4.7 | 1.7903 ± 0.486 | 3.2 ± 0.64 |
| 13 | L-(+)-Valine | 0.2 m | pH 2.4 | 1.492 ± 0.136 | 3.3 ± 0.13 |
| 14 | L-(+)-Valine | 0.2 m | pH 5.9 | 2.276 ± 0.396 | 3.9 ± 0.27 |
| 15 | L-(+)-Valine | 0.2 m | pH 9.6 | 1.760 ± 0.117 | 3.6 ± 0.13 |
| 16 | L-Leucine | 0.1 m | pH 2.4 | 1.567 ± 0.132 | 4.2 ± 0.09 |
| 17 | L-Leucine | 0.1 m | pH 6.0 | 1.083 ± 0.100 | 2.6 ± 0.50 |
| 18 | L-Leucine | 0.1 m | pH 9.7 | 1.462 ± 0.069 | 2.8 ± 0.371 |
| 19 | L-(−)-Isoleucine | 0.1 m | pH 2.4 | 0.921 ± 0.073 | 3.2 ± 0.28 |
| 20 | L-(−)-Isoleucine | 0.1 m | pH 6.0 | 3.167 ± 0.316 | 3.3 ± 0.19 |
| 21 | L-(−)-Isoleucine | 0.1 m | pH 9.7 | 0.797 ± 0.113 | 2.9 ± 0.77 |
| 22 | Glycine | 0.2 m | pH 2.4 | 0.557 ± 0.015 | 3.3 ± 0.09 |
| 23 | Glycine | 0.2 m | pH 6.0 | 0.532 ± 0.050 | 3.8 ± 0.13 |
| 24 | Glycine | 0.2 m | pH 9.6 | 1.003 ± 0.046 | 2.5 ± 0.59 |
| 25 | Control 40% Ethanol | — | — | 0.271 ± 0.049 | 1.5 ± 0.51 |

*Estimated Values

TABLE II

The Effect of Amino Acid on the Steady State Rate of Penetration of Levonorgestrel Through Hairless Mouse Skin

| Exp | Amino Acid | Molar Conc. | $J_{ss}$ (mcg/cm²/hr) | S.E.M. | n |
|---|---|---|---|---|---|
| a56, 87 | Tryptophan | 0.03 M | 0.6033 | 0.0380 | 12 |
| a56, 83 | Glutamic Acid | 0.03 M | 0.8277 | 0.1174 | 12 |
| a59, 75 | Glycine | 0.2 M | 0.8427 | 0.1008 | 16 |
| a56, 87 | Proline | 0.2 M | 0.8462 | 0.0768 | 12 |
| a59 | Alanine | 0.2 M | 0.8553 | 0.0736 | 4 |
| a59, 83 | Serine | 0.2 M | 0.8628 | 0.0883 | 12 |
| a56, 87 | Arginine | 0.2 M | 0.8864 | 0.0908 | 12 |
| a56 | Aspartic Acid | 0.2 M | 1.1538 | 0.1603 | 4 |
| a59, 71 | Leucine | 0.1 M | 1.3843 | 0.1039 | 15 |
| a59, 75 | Isoleucine | 0.1 M | 1.5542 | 0.2564 | 16 |
| a56, 83 | Cysteine | 0.2 M | 1.6160 | 0.1845 | 12 |
| a59, 71 | Valine | 0.2 M | 1.8006 | 0.1394 | 14 |

TABLE III

The Effect of Amino Acid at $pK_1'$ on the Steady State Rate of Penetration of Levonorgestrel through Hairless Mouse Skin

| Exp | Amino Acid | pH | $J_{ss}$ (mcg/cm²/hr) | S.E.M. |
|---|---|---|---|---|
| a75 | Glycine | 2.4 | 0.557 | 0.015 |
| a87 | Tryptophan | 3.2 | 0.641 | 0.078 |
| a87 | Arginine | 2.9 | 0.688 | 0.092 |
| a87 | Proline | 2.3 | 0.765 | 0.104 |
| a75 | Isoleucine | 2.4 | 0.921 | 0.073 |
| a71 | Valine | 2.4 | 1.492 | 0.136 |
| a71 | Leucine | 2.4 | 1.567 | 0.132 |
| a83 | Cysteine | 2.3 | 2.154 | 0.386 | n = 4

TABLE IV

The Effect of Amino Acid at pH 4 on the Steady State Rate of Penetration of Levonorgestrel through Hairless Mouse Skin

| Exp | Amino Acid | pH | $J_{ss}$ (mcg/cm²/hr) | S.E.M. |
|---|---|---|---|---|
| a56 | Trytophan | 4.7 | 0.6020 | 0.089 |
| a59 | Alanine | 4.8 | 0.8553 | 0.085 |
| a56 | Arginine | 4.2 | 0.9590 | 0.265 |
| a56 | Proline | 4.6 | 1.0863 | 0.161 |
| a59 | Serine | 4.7 | 1.1287 | 0.134 |
| a56 | Aspartic Acid | 4.4 | 1.1538 | 0.185 |
| a56 | Cysteine | 4.9 | 1.1635 | 0.092 |
| a56 | Glutamic Acid | 4.6 | 1.1910 | 0.227 |
| a59 | Glycine | 4.7 | 1.2790 | 0.284 |
| a59 | Isoleucine | 4.5 | 1.3328 | 0.276 |
| a59 | Leucine | 4.4 | 1.4451 | 0.358 |
| a59 | Valine* | 4.7 | 1.7903 | 0.486 | n = 4
*n = 3

TABLE V

The Effect of Amino Acid at Isoelectric pH on the Steady State Rate of Penetration of Levonorgestrel through Hairless Mouse Skin

| Exp. | Amino Acid | pH | $J_{ss}$ (mcg/cm²/hr) | S.E.M. |
|---|---|---|---|---|
| a75 | Glycine | 6.0 | 0.532 | 0.050 |
| a87 | Tryptophan | 6.5 | 0.567 | 0.050 |
| a87 | Proline | 6.7 | 0.688 | 0.066 |
| a83 | Glutamic Acid | 3.8 | 0.842 | 0.141 |
| a83 | Serine | 5.7 | 0.896 | 0.111 |
| a87 | Arginine | 10.8 | 1.012 | 0.016 |
| a71 | Leucine | 6.0 | 1.083 | 0.100 |
| a71 | Valine* | 5.9 | 2.276 | 0.396 |
| a75 | Isoleucine | 6.0 | 3.167 | 0.316 | n = 4
*n = 3

TABLE VI

The Effect of Amino Acid at $pK_2'$ on the Steady State Rate of Penetration of Levonorgestrel through Hairless Mouse Skin

| Exp. | Amino Acid | pH | $J_{ss}$ (mcg/cm²hr) | S.E.M. |
|---|---|---|---|---|
| a83 | Glutamic Acid | 9.9 | 0.450 | 0.045 |
| a83 | Serine | 9.1 | 0.564 | 0.098 |
| a75 | Isoleucine | 9.7 | 0.797 | 0.113 |
| a75 | Glycine | 9.6 | 1.003 | 0.046 |
| a87 | Arginine | 10.8 | 1.012 | 0.016 |
| a71 | Leucine* | 9.7 | 1.462 | 0.069 |
| a83 | Cysteine | 8.6 | 1.531 | 0.290 |
| a71 | Valine | 9.6 | 1.760 | 0.117 | n = 4
*n = 3

TABLE VII

The Effect of Net Charge on the Steady State Rate of Penetration of Levonorgestrel through Hairless Mouse Skin

VII A. Dibasic Amino Acid

| Amino Acid | pH | % Net Charge +1 | 0 | −1 | $J_{ss}$ mcg/cm²/hr | S.E.M. |
|---|---|---|---|---|---|---|
| Tryptophan | 3.2 | 13.3 | 86.7 | 0.0 | 0.641 | 0.078 |
| | 4.7 | 0.5 | 99.5 | 0.0 | 0.6020 | 0.089 |
| | 6.5 | 0.0 | 99.9 | 0.1 | 0.567 | 0.050 |
| Proline | 2.3 | 32.0 | 68.0 | 0.0 | 0.765 | 0.104 |
| | 4.6 | 0.2 | 99.8 | 0.0 | 1.0863 | 0.161 |
| | 6.7 | 0.0 | 99.99 | 0.0 | 0.688 | 0.066 |
| Glycine | 2.4 | 47.0 | 53.0 | 0.0 | 0.557 | 0.015 |
| | 4.7 | 0.4 | 99.6 | 0.0 | 1.2790 | 0.284 |
| | 6.0 | 0.0 | 100.0 | 0.0 | 0.532 | 0.050 |
| | 9.6 | 0.0 | 50.0 | 50.0 | 1.003 | 0.046 |
| Alanine | 4.8 | 0.3 | 99.7 | 0.0 | 0.8553 | 0.085 |
| Serine | 4.7 | 0.3 | 99.7 | 0.0 | 1.1287 | 0.134 |
| | 5.7 | 0.0 | 100.0 | 0.0 | 0.896 | 0.111 |
| | 9.1 | 0.0 | 53.0 | 47.0 | 0.564 | 0.098 |
| Leucine | 2.4 | 48.0 | 52.0 | 0.0 | 1.567 | 0.132 |
| | 4.4 | 1.0 | 99.0 | 0.0 | 1.4451 | 0.358 |
| | 6.0 | 0.02 | 99.95 | 0.03 | 1.083 | 0.100 |
| | 9.7 | 0.0 | 44.0 | 56.0 | 1.462 | 0.069 |
| Isoleucine | 2.4 | 48.0 | 52.0 | 0.0 | 0.921 | 0.073 |
| | 4.5 | 1.0 | 99.0 | 0.0 | 1.3328 | 0.276 |
| | 6.0 | 0.0 | 100.0 | 0.0 | 3.167 | 0.316 |
| | 9.7 | 0.0 | 49.0 | 51.0 | 0.797 | 0.113 |
| Valine | 2.4 | 45.0 | 55.0 | 0.0 | 1.492 | 0.136 |
| | 4.7 | 0.4 | 99.6 | 0.0 | 1.7903 | 0.486 |
| | 5.9 | 0.0 | 100.0 | 0.0 | 2.276 | 0.396 |
| | 9.6 | 0.0 | 51.0 | 49.0 | 1.760 | 0.117 |

VII B. Tribasic Amino Acid

| Amino Acid | pH | % Net Charge +1 | 0 | −1 | −2 | $J_{ss}$ mcg/cm²/hr | S.E.M. |
|---|---|---|---|---|---|---|---|
| Cysteine | 2.3 | 20.0 | 80.0 | 0.0 | 0.0 | 2.154 | 0.386 |
| | 4.9 | 0.06 | 99.9 | 0.04 | 0.0 | 1.1635 | 0.092 |
| | 8.6 | 0.0 | 40.0 | 60.0 | 0.4 | 1.531 | 0.290 |
| Glutamic Acid | 3.8 | 2.0 | 73.0 | 26.0 | 0.0 | 0.842 | 0.141 |
| | 4.6 | 0.1 | 31.0 | 69.0 | 0.0 | 1.1910 | 0.227 |
| | 9.9 | 0.0 | 0.0 | 37.0 | 63.0 | 0.450 | 0.045 |
| Aspartic Acid | 4.4 | 0.1 | 22.0 | 78.0 | 0.0 | 1.1538 | 0.185 |

VII C. Tribasic Amino Acid

| Amino Acid | pH | % Net Charge +2 | +1 | 0 | −1 | $J_{ss}$ mcg/cm²/hr | S.E.M. |
|---|---|---|---|---|---|---|---|
| Agrinine | 2.9 | 15.9 | 84.1 | 0.0 | 0.0 | 0.688 | 0.092 |
| | 4.2 | 0.9 | 99.1 | 0.0 | 0.0 | 0.9590 | 0.265 |
| | 10.8 | 0.0 | 1.7 | 96.3 | 2.0 | 1.012 | 0.016 |

TABLE VIII

The Effect of pH on the Average Rate of Penetration of Levonorgestrel through Hairless Mouse Skin in the Presence of Amino Acids

| pH | range | mcg/cm²/hr | S.E.M. | n |
|---|---|---|---|---|
| 2.5 | (2.3–3.2) | 1.0980 | 0.1073 | 32 |
| 4.5 | (3.8–4.9) | 1.1279 | 0.0668 | 51 |
| 6.1 | (5.7–6.7) | 1.2798 | 0.1894 | 27 |
| 9.6 | (8.6–10.8) | 1.0598 | 0.0891 | 31 |

TABLE IX

| Ex. No. | Amino Acid | Conc. | pH | Normalized* $J_{ss}$ (mcg/cm²/hr ± S.E.M.) |
|---|---|---|---|---|
| 26 | L-Norleucine | 0.05 m | 2.38 | 3.342 ± 0.5657 |
| 27 | L-Norleucine | 0.05 m | 6.09 | 2.483 ± 0.2185 |
| 28 | L-Norleucine | 0.05 m | 9.73 | 3.249 ± 0.5199 |
| 29 | L-Norvaline | 0.2 m | 2.37 | 4.278 ± 0.8765 |
| 30 | L-Norvaline | 0.2 m | 5.96 | 3.279 ± 1.236 |
| 31 | L-Norvaline | 0.2 m | 9.76 | 4.472 ± 1.165 |
| 32 | L-α-Amino-n-Butyric Acid | 0.2 m | 2.29 | 4.564 ± 0.7359 |
| 33 | L-α-Amino-n-Butyric Acid | 0.2 m | 6.03 | 2.556 ± 0.7365 |
| 34 | L-α-Amino-n-Butyric Acid exp. number a 119 | 0.2 m | 9.82 | 5.250 ± 0.6599 |

*Due to large differences in skin permeability between specimens it is necessary to run a reference standard in each transdermal experiment. The different rates of penetration for the reference standard are equated via an empirical proportionality constant. This constant is used to "normalize" the experiments to one another. Normalization is also used to compare results from experiments with different samples of skin from different species to account for high inter-species biological variation.

What is claimed is:

1. A pharmaceutical composition for transdermal administration of a steroidal contraceptive, comprising a steroidal contraceptive and an amount of an L-α-amino acid, selected from Tryptophan, Alanine, Proline, Serine, Cysteine, Glycine, Isoleucine, Leucine, Valine and α-Aminobutyric Acid, Norvaline and Norleucine, effective to enhance the penetration of said steroidal contraceptive through the skin, dispersed in a transdermally effective carrier.

2. A pharmaceutical composition for transdermal administration of claim 1 in which the steroidal contraceptive includes Levo-norgestrel, Ethinyl Estradiol or 17-Beta-estradiol.

3. A pharmaceutical composition for transdermal administration of claim 1 in which the L-α-amino acid is selected from Valine, Cysteine, Isoleucine, Leucine and α-Aminobutyric Acid.

4. A pharmaceutical composition for transdermal administration of claim 1 in which the transdermally effective carrier comprises a matrix.

5. A method for enhancing the rate of penetration through the skin of a steroidal contraceptive contained in a pharmaceutical composition for transdermal administration, said composition comprising such steroidal contraceptive dispersed in a transdermally effective carrier, said method characterized in including in said transdermal composition an amount of an L-α-amino acid, selected from Tryptophan, Alanine, Proline, Serine, Cysteine, Glycine, Isoleucine, Leucine, Valine, α-Aminobutyric Acid, Norvaline and Norleucine effective to enhance the penetration of said steroidal contraceptive through the skin.

6. A method of claim 5 in which the steroidal contraceptive includes Levo-Norgestrel, Ethinyl Estradiol or 17-Beta-estradiol.

7. A method of claim 5 in which the L-α-amino acid is selected from Valine, Cysteine, Isoleucine, Leucine and α-Aminobutyric Acid.

8. A method of claim 5 in which the transdermally effective carrier comprises a matrix.

* * * * *